(12) United States Patent
Deacon et al.

(10) Patent No.: US 7,621,949 B2
(45) Date of Patent: Nov. 24, 2009

(54) FOLDABLE INTRAOCULAR LENS AND METHOD OF MAKING

(75) Inventors: Jim Deacon, Goleta, CA (US); David J. Shepherd, San Juan Capistrano, CA (US); Daniel G. Brady, San Juan Capistrano, CA (US); Marlene L. Paul, Laguna Niguel, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 889 days.

(21) Appl. No.: 11/010,003

(22) Filed: Dec. 9, 2004

(65) Prior Publication Data

US 2005/0125056 A1    Jun. 9, 2005

Related U.S. Application Data

(60) Provisional application No. 60/528,273, filed on Dec. 9, 2003.

(51) Int. Cl.
   *A61F 2/16*    (2006.01)
(52) U.S. Cl. .................................................. 623/6.49
(58) Field of Classification Search ................ 623/6.16, 623/6.17, 6.19, 6.43, 6.46, 6.49
   See application file for complete search history.

(56) References Cited

U.S. PATENT DOCUMENTS

| | | | |
|---|---|---|---|
| 3,034,403 A | 5/1962 | Neefe |
| 3,454,332 A | 7/1969 | Siegel |
| 4,173,798 A | 11/1979 | Welsh |
| 4,244,060 A | 1/1981 | Hoffer |
| 4,370,760 A | 2/1983 | Kelman |
| 4,377,873 A | 3/1983 | Reichert, Jr. |
| 4,412,359 A | 11/1983 | Myers |
| 4,418,431 A | 12/1983 | Feaster |

(Continued)

FOREIGN PATENT DOCUMENTS

EP    0186634    7/1986

(Continued)

OTHER PUBLICATIONS

Accession No. EIX94061902761, Published Nov. 6, 1993, Osborn, D.C., Development of a foldable composite hydrogel intraocular lens.

(Continued)

*Primary Examiner*—William H. Matthews

(57) ABSTRACT

A foldable intraocular lens for providing vision contains an optic body that includes an optical zone and a peripheral zone entirely surrounding the optical zone. The optic body has an anterior face, a substantially opposing posterior face, an optic edge, and an optical axis. The anterior face comprises a central face, a peripheral face, and a recessed annular face therebetween that is disposed posterior to the peripheral face. The intraocular lens further comprises at least one haptic that is integrally formed with the peripheral zone. The haptic comprises a distal posterior face, a proximal posterior face, and a step edge disposed at a boundary therebetween. The haptic further comprises a side edge disposed between the optic edge and the step edge. The proximal posterior face and the posterior face of the optic body form a continuous surface. An edge corner is formed by the intersection of the continuous surface with the optic edge, the side edge, and the step edge.

25 Claims, 4 Drawing Sheets

U.S. PATENT DOCUMENTS

| | | |
|---|---|---|
| 4,435,856 A | 3/1984 | L'Esperance |
| 4,449,257 A | 5/1984 | Koeniger |
| 4,576,607 A | 3/1986 | Kelman |
| 4,585,455 A | 4/1986 | Blackmore et al. |
| 4,601,722 A | 7/1986 | Kelman |
| 4,605,409 A | 8/1986 | Kelman |
| 4,629,460 A | 12/1986 | Dyer |
| 4,661,108 A | 4/1987 | Grendahl et al. |
| 4,664,665 A | 5/1987 | Reuss et al. |
| 4,676,791 A | 6/1987 | Lemaster et al. |
| 4,702,244 A | 10/1987 | Mazzocco |
| 4,704,123 A | 11/1987 | Smith |
| 4,710,195 A | 12/1987 | Giovinazzo |
| 4,743,254 A | 5/1988 | Davenport |
| 4,781,717 A | 11/1988 | Grendahl |
| 4,808,181 A | 2/1989 | Kelman |
| 4,863,465 A | 9/1989 | Kelman |
| 4,878,912 A | 11/1989 | Castleman |
| 4,898,461 A | 2/1990 | Portney |
| 4,990,159 A | 2/1991 | Kraff |
| 5,002,571 A | 3/1991 | O'Donnell, Jr. et al. |
| 5,074,875 A | 12/1991 | Donn et al. |
| 5,076,684 A | 12/1991 | Simpson et al. |
| 5,078,740 A | 1/1992 | Walman |
| 5,089,023 A | 2/1992 | Swanson |
| 5,133,749 A | 7/1992 | Nordan |
| 5,171,320 A | 12/1992 | Nishi |
| 5,180,390 A | 1/1993 | Drews |
| 5,197,981 A | 3/1993 | Southard |
| 5,201,763 A | 4/1993 | Brady et al. |
| 5,217,491 A | 6/1993 | Vanderbilt |
| 5,300,117 A | 4/1994 | Baikoff et al. |
| 5,366,501 A | 11/1994 | Langerman |
| 5,370,687 A | 12/1994 | Poler |
| 5,376,115 A | 12/1994 | Jansen |
| 5,405,385 A | 4/1995 | Meimke et al. |
| 5,405,386 A | 4/1995 | Rheinish et al. |
| 5,476,513 A | 12/1995 | Brady et al. |
| 5,549,670 A | 8/1996 | Young et al. |
| 5,578,078 A | 11/1996 | Nakajima et al. |
| 5,674,283 A | 10/1997 | Stoy |
| 5,693,093 A | 12/1997 | Woffinden et al. |
| 5,693,094 A | 12/1997 | Young et al. |
| 5,716,403 A | 2/1998 | Tran et al. |
| 5,755,786 A | 5/1998 | Woffinden et al. |
| 5,928,282 A | 7/1999 | Nigam |
| 6,162,249 A | 12/2000 | Deacon et al. |
| 6,179,870 B1 | 1/2001 | Sourdille et al. |
| 6,190,410 B1 | 2/2001 | Lamielle et al. |
| 6,228,115 B1 | 5/2001 | Hoffmann et al. |
| 6,398,809 B1 | 6/2002 | Hoffmann et al. |
| 6,461,384 B1 | 10/2002 | Hoffmann et al. |
| 6,468,306 B1 | 10/2002 | Paul et al. |
| 6,469,306 B1 | 10/2002 | Van Dulmen et al. |
| 6,488,709 B1 | 12/2002 | Barett |
| 6,506,212 B2 * | 1/2003 | Zhou et al. .......... 623/6.38 |
| 6,596,025 B2 | 7/2003 | Portney |
| 6,609,793 B2 | 8/2003 | Norrby et al. |
| 6,685,741 B2 | 2/2004 | Landreville et al. |
| 6,692,525 B2 | 2/2004 | Brady et al. |
| 6,786,928 B2 | 9/2004 | Callahan |
| 6,800,091 B2 | 10/2004 | Callahan |
| 6,827,738 B2 | 12/2004 | Willis |
| 6,849,091 B1 | 2/2005 | Cumming |
| 6,921,415 B2 | 7/2005 | Callahan |
| 6,926,744 B1 | 8/2005 | Bos |
| 7,014,656 B2 | 3/2006 | Galin |
| 2002/0087210 A1 | 7/2002 | Stenger et al. |
| 2003/0055499 A1 | 3/2003 | Nguyen et al. |
| 2003/0120342 A1 | 6/2003 | Green |
| 2003/0130733 A1 | 7/2003 | Deacon et al. |
| 2003/0171807 A1 | 9/2003 | Pham et al. |
| 2003/0199976 A1 | 10/2003 | Portney |
| 2003/0204257 A1 | 10/2003 | Southard |
| 2004/0002757 A1 | 1/2004 | Lai et al. |
| 2004/0024454 A1 | 2/2004 | Troop |
| 2005/0015143 A1 | 1/2005 | Willis |
| 2005/0021140 A1 | 1/2005 | Liao |
| 2005/0033421 A1 | 2/2005 | Toop |
| 2005/0085907 A1 | 4/2005 | Hanna |
| 2005/0119740 A1 | 6/2005 | Esch |
| 2005/0119741 A1 | 6/2005 | Cumming |
| 2005/0125055 A1 | 6/2005 | Deacon et al. |
| 2005/0125059 A1 | 6/2005 | Pinchuk |
| 2005/0192667 A1 | 9/2005 | Schachar |
| 2005/0246017 A1 | 11/2005 | Messner |
| 2006/0041308 A1 | 2/2006 | Nichamin |
| 2006/0052869 A1 | 3/2006 | Reed |
| 2006/0064162 A1 | 3/2006 | Klima |
| 2006/0069432 A1 | 3/2006 | Tran |
| 2006/0095127 A1 | 5/2006 | Feingold |
| 2006/0122700 A1 | 6/2006 | Kurosaka |
| 2006/0142855 A1 | 6/2006 | Vaudant |

FOREIGN PATENT DOCUMENTS

| | | |
|---|---|---|
| EP | 0195881 | 10/1986 |
| EP | 0215468 | 3/1987 |
| EP | 0246754 | 11/1987 |
| EP | 0255759 | 2/1988 |
| EP | 0268569 | 5/1988 |
| EP | 0326373 | 8/1989 |
| EP | 0404478 | 12/1990 |
| EP | 0458508 | 8/1992 |
| EP | 0336877 B1 | 10/1993 |
| EP | 0579528 | 1/1994 |
| EP | 507292 | 7/1997 |
| EP | 0457553 | 1/1999 |
| EP | 599457 | 5/1999 |
| EP | 0566461 B1 | 8/1999 |
| EP | 1194084 B1 | 12/2004 |
| EP | 1502561 | 2/2005 |
| FR | 2655842 | 6/1991 |
| FR | 2661816 | 11/1991 |
| FR | 2701390 | 8/1994 |
| FR | 2858544 | 2/2005 |
| GB | 2111835 | 7/1983 |
| GB | 2171912 | 9/1986 |
| GB | 2181355 | 4/1987 |
| JP | 406218001 | 8/1994 |
| WO | WO 89/09576 | 10/1989 |
| WO | WO9215260 | 9/1992 |
| WO | WO 93/00204 | 1/1993 |
| WO | WO9506446 | 3/1995 |
| WO | WO 97/33536 | 9/1997 |
| WO | WO 03/059208 A2 | 7/2003 |
| WO | WO 03/077803 | 6/2004 |
| WO | WO 2004/082535 | 9/2004 |
| WO | WO 2005/032427 | 4/2005 |
| WO | WO 2004/096099 | 7/2005 |
| WO | WO 2005/082286 | 9/2005 |

OTHER PUBLICATIONS

Accession No. PREV199396057867, Published May 1993, Menapace, Exchange of IOGEL hydrogel one-piece foldable intraocular lens for bag-fixated J-loop poly(methyl methacrylate) intraocular lens.

ACRIMED *One-piece posterior chamber lens for capsular bag fixation*. ACRIMED. One page.

Apple, D. J., M.D. Will PCO soon be a concern of the past? *Ocular Surgery News*. vol. 17. 1999. p. 44.

Beiting. Down the line: pharmaceutical solutions to the PCO problem. *Eye World*. Jun. 1999. 2 pages.

Brunette, D. M. Spreading and orientation of epithelial cells on grooved substrata. *Experimental Cell Research*. vol. 167. 1986. pp. 203-217.

Charters, L. High refractive errors can be improved with IOLs. *Ophthalmology Times*. Jun. 1999. p. 14.

Choyce, Rayner & Keeler Limited, Catalogue No. 469, Jul. 1978, 3 pages.

Coombers, A., and Seward, H. Posterior capsular opacification prevention: IOL design and material. *Br J Opthalmol* vol. 83. 1999. pp. 640-641.

Guttman, C. Square-edge silicone IOL strikingly prevents PCO. *Ophthalmology Times*. Jun. 1999. p. 14.

Holladay, J.T. M.D., Msee, Lang, A. PhD., and Portney, V., PhD. Analysis of edge glare phenomena in intraocular lens edge designs. *Journal of Cataract Refractive Surgery*. vol. 25. Jun. 1999. pp. 748-752.

Martin, R. G. Effect of posterior chamber intraocular lens design and surgical placement on postoperative outcome. *Journal of Cataract Refractive Surgery*, vol. 18, Jul. 1992, pp. 333-341.

Masket, S. M.D., et. al. Undesired light images associated with ovoid intraocular lenses. *Journal of Cataract Refractive Surgery*. vol. 19. Nov. 1993. pp. 690-694.

Nagata, T. and Watanabe, I. Optic sharp edge or convexity: comparison of effects on posterior capsular opacification. *Japanese Journal of Ophthalmology*, vol. 40, 1996, pp. 397-403.

Nishi, O., M.D. Square-edged optics of both acrylic and PMMA inhibited PCO in experimental study. *New Ocular Surgery*. Jul. 1999. p. 45.

Nishi, O., M.D., and Nishi, K., M.D. Preventing posterior capsule opacification by creating a discontinuous sharp bend in the capsule. *Journal of Cataract Refractive Surgery*. vol. 25. Apr. 1999. pp. 521-526.

Peng et al. Chicago Ophthalmology Society Meeting held Oct. 20-21, 1997. pp. 1-26.

Waller, S. M.D., and Steinert, R. F. M.D. Symptomatic intraocular reflections from oval intraocular lens implants. *American Journal of Ophthalmology*. Sep. 1993. pp. 374-376.

Miho Sugita et al., American Journal of Ophthalmology, Magazine, Feb. 2004, vol. 137, No. 2, pp. 377-379.

\* cited by examiner

US 7,621,949 B2

FOLDABLE INTRAOCULAR LENS AND METHOD OF MAKING

RELATED APPLICATION

The present application claims priority under 35 U.S.C §119(e) to provisional application No. 60/528,273, filed on Dec. 9, 2003, under the same title. Full Paris Convention priority is hereby expressly reserved.

BACKGROUND OF THE INVENTION

1. Field of the Invention

This invention relates generally to a foldable intraocular lens and more specifically to a foldable intraocular lens having at least one integrally formed haptic with a step edge configured to reduce posterior capsule opacification (PCO), stabilize the intraocular lens, and/or reduce the volume of the intraocular lens.

2. Description of the Related Art

Foldable ophthalmic lenses, such as intraocular lenses (IOLs), are used to replace the natural lens of an eye, for instance, when the natural lens is removed due to cataracts. Three-piece IOLs typically comprise an optic made of a soft, foldable material into which stiffer fixation members or haptics are staked to provide centering and stabilization of the lens. One-piece IOLs are also available in which the haptics or fixation members are integrally formed with the optic from the same foldable material as the optic.

One problem found with IOLs implanted in the capsular bag is that of posterior capsular opacification (PCO), a condition in which remnant equatorial lens epithelial cells (LECs) migrate between the posterior capsule surface and the posterior surface of the IOL. The incidence of PCO may be reduced by providing a continuous, sharp posterior corner around the entire posterior surface of the optic to impede cell migration into the lens area (e.g., U.S. Pat. Nos. 6,162,249 and 6,468,306, which are herein incorporated by reference). However, in the case of one-piece IOLs, haptic materials are generally soft, resulting in relatively bulky haptics that are thought to compromise the blockage of cell growth into the lens area. The haptics are especially bulky proximal to the lens, where greater rigidity is used to support the haptics and to help prevent the distal portions of haptics from sticking to the optic after insertion into the eye. Therefore, despite the use of sharp, square optic edges, the bulky haptics used in one-piece IOLs can lead to an increased incidence of PCO, as compared to similar three-piece IOLs (Miho Sugita, et al., American Journal of Ophthalmology, February 2004, vol. 137, no. 2, pp 377-379).

One reason for the increased prevalence of PCO in one-piece IOLs is thought to be that the relatively bulky haptics present an obstacle in attachment of the anterior capsule with the posterior capsule. This "shrink-wrap" effect may be advantageously used to pull the posterior capsule surface tight against the sharp posterior corner of the IOL. Ideally, the best corner seal should occur when there are no haptics present at all. The bulky haptics of a one-piece IOL move further from this ideal than the smaller haptic generally used in three-piece IOLs, thus providing a possible explanation of the higher incidence of PCO for one-piece IOLs.

In certain designs, a step edge is also formed on the optic in the vicinity of the haptics, providing in a continuous, 360 degree circular edge seal that surrounds the center of the lens and the posterior capsule. While this 360 degree edge seal configuration is relatively straightforward to implement in three-piece IOLs, it is more difficult for one-piece IOLs, since construction of an effective step edge in the area of the haptics can compromise other IOL design parameters. For instance, if the optic edge is made relatively thin, in order to reduce overall IOL volume, the haptic may be too thin to provide a desired amount of stiffness if a step edge is incorporated. Conversely, if the optic edge is made relatively thick, in order to provide a suitable attachment area for a thicker, stiffer haptic and to allow room for a suitable step edge, then the overall IOL volume may be too large, potentially leading to undesirably large incisions in the eye.

One way of helping to decrease the total IOL volume is disclosed in U.S. Pat. No. 5,476,513 to Brady et al., which is herein incorporated by reference. The '513 patent teaches an IOL having an optical zone surrounded by a peripheral zone, wherein the peripheral zone is thicker than the adjacent periphery of optical zone. Using this construction, the inlaid optical zone may be made thinner than it might otherwise be in an equivalent IOL not having a thicker peripheral zone. One potential problem with such an inlaid optical zone is that relatively sharp corners can contribute to undesired optical effects such as halos or visual poor contrast (e.g., FIG. 3A of the '513 patent). Such a design approach also does not address the problem of PCO.

Therefore, one-piece IOLs are needed that are simultaneously resistant to PCO, have an overall volume that is sufficiently small for delivery through a relatively small ocular incision, and produce a low level of scattered light.

SUMMARY OF THE INVENTION

The present invention is directed to an intraocular lens that may be placed in the posterior chamber of a mammalian eye, comprising an optical zone and an integrally formed haptic with a step edge that is contiguous around the entire posterior edge of the optical zone. As discussed in greater detail below herein, the intraocular lens provides both a high resistance to the migration of LECs under the posterior optic surface and an overall volume that is sufficiently small for delivery through a relatively small ocular incision.

One aspect of the invention involves a foldable intraocular lens containing an optic body that includes an optical zone and a peripheral zone entirely surrounding the optical zone. The optic body has an anterior face, a substantially opposing posterior face, an optic edge, and an optical axis. The anterior face comprises a central face, a peripheral face, and a recessed annular face therebetween that is disposed posterior to the peripheral face. The intraocular lens further comprises at least one haptic that is integrally formed with the peripheral zone. The haptic comprises a distal posterior face, a proximal posterior face, and a step edge disposed at a boundary therebetween. The haptic further comprises a side edge disposed between the optic edge and the step edge. The proximal posterior face and the posterior face of the optic body form a continuous surface. An edge corner is formed by the intersection of the continuous surface with the optic edge, the side edge, and the step edge. The distal posterior face may be substantially perpendicular to the optical axis or disposed at an angle relative to a plane perpendicular to the optical axis. In the later case, the angle is preferably in the range of about 2 degrees to about 12 degrees or greater.

The haptic may be characterized by a haptic thickness that is equal to a distance along the optical axis that is between the distal posterior face and a substantially opposing haptic anterior face. The haptic thickness is preferably greater than or approximately equal to an optic edge thickness along the optical axis. In one embodiment, at least one of the haptic thickness or the optic edge thickness along the optical axis is in the range of at least about 0.4 mm or less to about 0.5 mm or more. At least a portion of step edge may be configured to form a substantially straight line and/or an arcuate shape. In certain embodiments, the step edge tapers radially, while in other embodiments at least a portion of step edge forms a rounded tip and/or varies in thickness along the optical axis. At least a portion of the step edge may conform to a side of the haptic.

In another aspect of the invention, the step edge has a height H and the optic edge has a thickness T, and the height H is much less than the thickness T. For example, the height H may be about 0.1 mm, while the thickness T may be in the range of about 0.4 mm or less to about 0.5 mm or more. Alternatively, the height H may be slightly less than, greater than, or approximately equal the thickness T.

In yet another aspect of the invention, at least a portion of the peripheral face is disposed at an angle relative to a plane perpendicular to the optical axis that is preferably in the range of about 5 degrees to at least about 50 degrees in certain embodiments and in the range of about 15 degrees to about 35 degrees in other embodiments.

Another aspect of the invention involves a foldable intraocular lens that comprises an optic body that includes an optical zone and a peripheral zone entirely surrounding the optical zone. The optic body has an anterior face, a substantially opposing posterior face, an optic edge, and an optical axis. The intraocular lens further comprises at least one haptic integrally formed with the peripheral zone containing a distal posterior face, a proximal posterior face, a step edge disposed at a boundary between the proximal posterior face and the distal posterior face, and a side edge disposed between the optic edge and the step edge. The proximal posterior face and the posterior face of the optic body form a continuous surface and the edge corner is formed by the intersection of the continuous surface with the optic edge, the side edge, and the step edge. The distal posterior face of the intraocular lens is perpendicular to the optical axis. Preferably, the haptic further comprises an anterior face that is also perpendicular to the optical axis.

Still another aspect of the invention involves a foldable intraocular lens that comprises an optic body that includes an optical zone and a peripheral zone entirely surrounding the optical zone. The optic body has an anterior face, a substantially opposing posterior face, an optic edge, and an optical axis. The anterior face comprises a central face, a peripheral face, and a recessed annular face therebetween disposed posterior to the peripheral face. The intraocular lens further comprises a cross-sectional profile formed in a plane that passes through the optical axis. The cross-sectional profile includes the intersection of the plane with the recessed annular face and the peripheral face. The cross-sectional profile is continuous, smooth, and free of discontinuities. The cross-sectional profile may further include the optic edge. In certain embodiments, the cross-sectional profile consists of a plurality of arcuate sections. At least a portion of the cross-sectional profile may comprise a line portion disposed at an acute angle with a line that is parallel to the optical axis.

Yet another aspect of the invention involves a method of making a foldable intraocular lens. The method comprises providing an optic body including an optical zone and a peripheral zone entirely surrounding the optical zone, the optic body having an anterior face, a substantially opposing posterior face, an optic edge, and an optical axis. The anterior face comprises a central face, a peripheral face, and a recessed annular face therebetween that is disposed posterior to the peripheral face. The method further comprises integrally forming, at the peripheral zone, at least one haptic comprising a distal posterior face, a proximal posterior face, and a step edge disposed at a boundary therebetween. The method further comprises forming a side edge disposed between the optic edge and the step edge, forming the proximal posterior face and the posterior face of the optic body into a continuous surface, and forming an edge corner comprising the intersection of the continuous surface with the optic edge, the side edge, and the step edge.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following five figures, with like numerals indicating like parts.

DETAILED DESCRIPTION OF THE DRAWINGS

Figure 1:
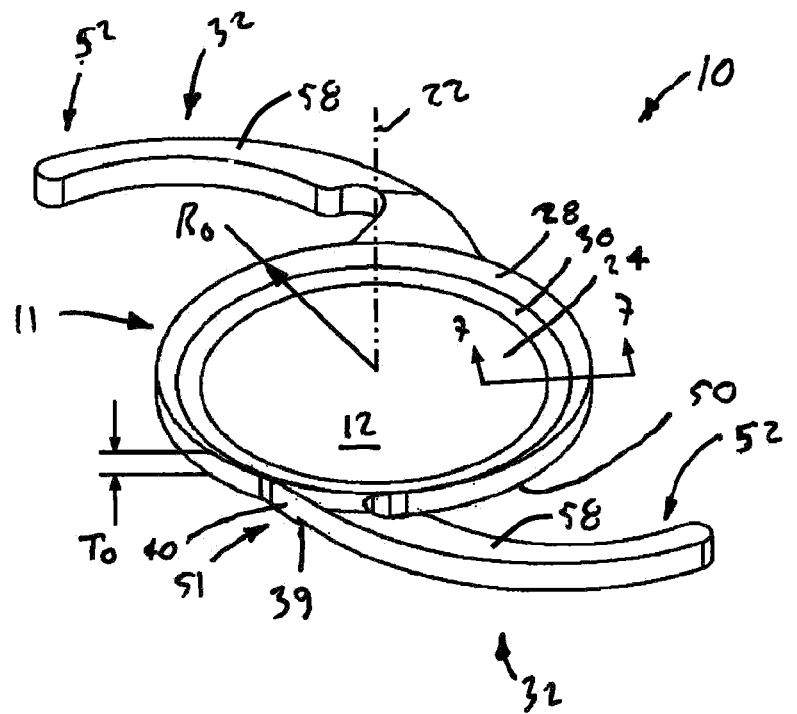
FIG. 1 is a perspective view illustrating the anterior surface of an intraocular lens according to one embodiment of the present invention.
Figure 2:
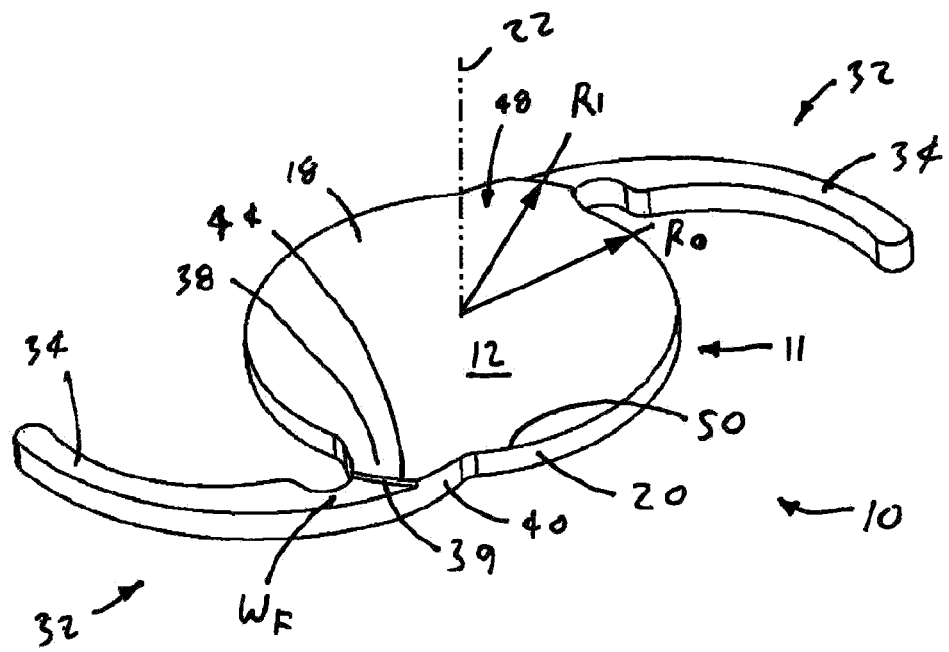
FIG. 2 is a perspective view illustrating the posterior surface of the intraocular lens shown in FIG. 1.
Figure 3:
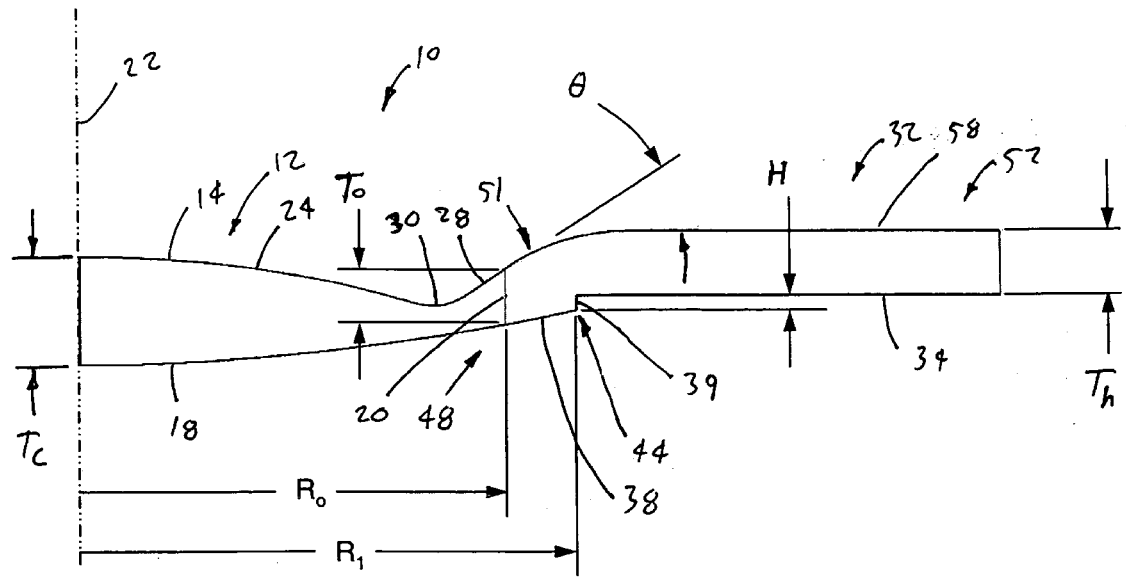
FIG. 3 is a side view of a portion of the intraocular lens shown in FIG. 1.

As illustrated in FIGS. 1-3, in certain embodiments, a foldable intraocular lens 10 comprises an optic body 11 including an optical zone 12 and a peripheral zone 13 entirely surrounding the optical zone 12. The optic body 11 has an anterior face 14, a substantially opposing posterior face 18, an optic edge 20, and an optical axis 22. The anterior face 14 comprises a central face 24, a peripheral face 28, and a recessed annular face 30 therebetween that is disposed posterior to the peripheral face 28. The intraocular lens 10 further comprises at least one haptic 32 that is integrally formed with the peripheral zone 13. The haptic 32 comprises a distal posterior face 34, a proximal posterior face 38, and a step edge 39 disposed at a boundary therebetween. The haptic further comprises a side edge 40 disposed between the optic edge 20 and the step edge 39. The proximal posterior face 38 and the posterior face 18 of the optic body 11 form a continuous surface 48. An edge corner 50 is formed by the intersection of the continuous surface 48 with the optic edge 20, the side edge 40, and the step edge 39.

The optic body 11 is preferably generally circular having a radius $R_o$ and may be constructed of at least one of the materials commonly used for resiliently deformable or foldable optics, such as silicone polymeric materials, acrylic polymeric materials, hydrogel polymeric materials, such as polyhydroxyethylmethacrylate, polyphosphazenes, polyurethanes, and mixtures thereof and the like. Alternatively, the optic body 11 may be constructed of at least one of the commonly employed material or materials used for rigid optics, such as polymethylmethacrylate (PMMA). In a preferred embodiment, the optic body 11 is made of SENSAR® brand of acrylic. Other advanced formulations of silicone, acrylic, or mixtures thereof are also anticipated. The optic body 11 material is preferably selected such that the optical zone 12 is optically clear and exhibits biocompatibility in the environment of the eye. Selection parameters for suitable lens materials are well known to those of skill in the art. See, for example, David J. Apple, et al., Intraocular Lenses. Evolution, Design, Complications, and Pathology, (1989) William & Wilkins. Foldable/deformable materials are particularly advantageous since optics made from such deformable materials may be rolled, folded or otherwise deformed and inserted into the eye through a small incision. The lens material preferably has a refractive index allowing a relatively thin, and preferably flexible optic section, for example, having a center thickness in the range of about 150 microns to about 1000 microns, depending on the material and the optical power of the optic body 11. For example, in one embodiment, the optic body 11 is made of Sensar® brand of acrylic and an optical power of 20D. In such embodiment, the optical zone 12 has a center thickness $T_c$ that is preferably in the range of about 0.5 mm or less to about 1.0 mm or more, more preferably in the range of about 0.7 mm to about 0.9 mm. The center thickness $T_c$ may vary from these ranges depending on factors such as the lens material and the dioptric power of the optical zone 12. The optic body 11 preferably has a diameter of at least about 4 mm to about 7 mm or more, more preferably about 5 mm to about 6.5 mm or about 6.0 mm. As used herein the term "thickness" generally refers to a dimension of a portion or feature of the intraocular lens 10 as measured substantially along the optical axis 22.

The intraocular lens 10 may comprise any of the various means available in the art for centering or otherwise locating the optical zone 12 within the eye. For example, as illustrated in FIGS. 1-3, the intraocular lens 10 may comprise one or more fixation members or haptics 32. The haptics 32 are preferably integrally made of the same material as the optic body 11 so as to form a one-piece IOL. Alternatively, the haptics 32 may be integrally formed in a common mold with the optic body 11, but be made of a different material than the optic body 11. In other instances, the haptics 32 formed of the same material as the optic body 11, but haptics 32 and the optic body 11 materials have different states, for instance differing amounts of water content or percentage of cross-linked polymer. In yet other embodiments, the haptics may be formed separately from the optic body 11 and attached to the optic body 11 to provide a three-piece configuration. In such configurations, the haptics 32 may comprise any of a variety of materials which exhibit sufficient supporting strength and resilience, and which are substantially biologically inert in the intended in vivo or in-the-eye environment. Suitable materials for this purpose include, for example, polymeric materials such as polypropylene, PMMA, polycarbonates, polyamides, polyimides, polyacrylates, 2-hydroxymethylmethacrylate, poly (vinylidene fluoride), polytetrafluoroethylene and the like; and metals such as stainless steel, platinum, titanium, tantalum, shape-memory alloys, e.g., nitinol, and the like. In other embodiments, the intraocular lens 10 comprises a positioning means that allows the optic body 11 to move along the optical axis 22 or be deformed in response to deformation of the capsular bag and/or in response to the ciliary muscles of the eye.

The optical zone 12 may take any of the forms known in the art. For example the optical zone 12 may be biconvex, plano-convex, plano-concave, meniscus, or the like. The optical power of the optical zone 12 may be either positive or negative. The general profile or shape of the posterior face 18 and the central face 24 of the optic zone 12 may be any used for producing an optic based on refraction of incident light. For instance, the posterior face 18, the central face 24, or both faces 18, 24 may be spherical with an overall radius of curvature that is either positive or negative. Alternatively, the profile or shape of either the posterior face 18, the central face 24, or both faces 18, 24 may be parabolic or any aspheric shape common in the art for reducing aberrations such as spherical aberrations. For example, the posterior face 18 or the central face 24 may be an aspheric surface designed to reduce spherical aberrations based on either an individual cornea or group of corneas as described by Piers et al. in U.S. Pat. No. 6,609,673 and U.S. patent application Ser. Nos. 10/119,954, 10/724,852, herein incorporated by reference. Other aspheric and asymmetric surface profiles of the posterior face 18 or the central face 24 of use within the art are also consistent with embodiments of the intraocular lens 10. The posterior face 18 or the central face 24 may alternatively be configured to provide more than one focus, for example to correct for both near and distant vision as described by Portney in U.S. Pat. No. 4,898,461.

At least portions of the posterior face 18, the central face 24, or both faces 18, 24 of the optical zone 12 may comprise one or more optical phase plates. In such embodiments, the total optical power of the optical zone 12 is a combination of the refractive power of the posterior face 18 and the central face 24, and the optical power of the one or more diffraction orders produced by the one or more phase plates. The one or more phase plates may be either a monofocal phase plate providing one dominant diffraction order or a multifocal phase plate, such as a bifocal phase plate, for providing, for instance, simultaneous near and distant vision. Other types of phase plates may also be used. For example, the phase plate may be based on a change in the refractive index of the material used to form the optical zone 12.

The total optical power of the optical zone 12 is preferably within a range of at least about +2 Diopters to about +50 Diopters or more, more preferably within a range of about +5 Diopters to about +40 Diopters, and most preferably a range of about +5 Diopters to about +30 Diopters. The total optical power may be either positive or negative, for instance within a range of about −15 Diopters or less to about +15 Diopters or more, or within a range of about −10 Diopters to about +10 Diopters. Other ranges of refractive optical power may be preferred, depending on the particular application and type of intraocular lens to be used.

In certain embodiments, the haptics 32 are characterized by a haptic thickness $T_h$ that is equal to a distance, as measured along the optical axis 22, between the distal posterior face 34 of the haptic 32 and the substantially opposing anterior face 58. Preferably, the haptic thickness $T_h$ is greater than or approximately equal to a thickness $T_o$ of the optic edge 20, as measured along the optical axis 22. The thicknesses $T_h$ and $T_o$ may be selected based on the particular material from which the intraocular lens 10 is made, the amount of rigidity desired, the optical power of the lens 10, and other such factors. In one embodiment, at least one of the haptic thickness $T_h$ and the optic edge thickness $T_o$, is preferably in the range of about 0.2 mm or less to about 1 mm or more, more preferably in the range of about 0.3 mm to about 0.6 mm, and even more preferably in the range of about 0.4 mm to about 0.5 mm.

The step edge 39 is disposed between the proximal posterior face 38 and distal posterior face 34 of each haptic 32. The step edge 39 is part of the edge corner 50 that forms a continuous boundary around the posterior face 18 of the optic body 11 to help prevent PCO. In certain embodiments, the step edge 39 has a height H that is preferably in the range of about 0.05 mm or less to about 1 mm or more, more preferably in the range of about 0.05 mm to about 0.2 mm. In other embodiments, the step edge 39 has a height H that is in the range of about 0.2 mm to about 0.5 mm.

As a result of the step edge 39, the distal posterior face 34 of each haptics 32 has an anterior offset relative to the proximal posterior face 38. In certain embodiments, the step edge 39 has a height H that is much less than the optic edge thickness $T_o$. For example, the height H may be about 0.1 mm and the optic edge thickness $T_o$ may be in the range of about 0.4 mm or less to about 0.5 mm or more. Alternatively, in other embodiments, the height H is greater than or approximately equal to the optic edge thickness $T_o$. The height H may be selected based on various design parameters, including, the particular material from which the intraocular lens 10 is made, the amount of rigidity desired in the haptics 32, and other such factors. Preferably, height H is selected sufficiently large so that the integrity of the contact of the edge corner 50 with the posterior capsule of the eye is maintained so as to help avoid PCO.

In certain embodiments, at least a portion of the step edge 39 is a straight line and is substantially disposed at a radius $R_1$ from the optical axis 22. Alternatively or additionally, at least a portion of the step edge 39 may be arcuate in shape. The radius $R_1$ is advantageously greater than the radius $R_o$ of the optic edge 20 so that a proximal portion of the haptic 32 forms a buttress 51 that is preferably thicker than a distal portion 52 of the haptic 32 and the edge thickness $T_o$. The buttress 51 of each haptic 32 provides greater haptic rigidity in the vicinity of the peripheral zone 13, resulting in a biasing force that biases the distal portion 52 of the haptic 32 away from the optical zone 12. The biasing force away from the optical zone 12 can favorably act to reduce the tendency of the haptics 32 to stick to the optical zone 12. Such sticking problems have been noted with certain one-piece IOL materials that are both soft and tacky. Another potential benefit of the step edge 39 is that the thickness of the distal portion 52 of each haptic 32 $T_h$ may be fabricated to be less than the thickness of the buttress 51, thus reducing the total volume of the intraocular lens 10 and permitting a smaller incision in the eye to be used during surgery. The greater haptic rigidity in the vicinity of the peripheral zone 13 of the optic body 11 also results in a radial force for centering the intraocular lens 10 within the eye and provides an axial force, as explained below herein. The axial force pushes the edge corner 50 that surrounds the posterior face 18 against the posterior capsule of the eye to help prevent PCO. Disposing the step edge 39 at a radius $R_1$ that is greater than $R_o$ provides yet another potential advantage. The greater rigidity provided by the buttress 51 permits the creation of a flex point $W_f$ near the peripheral zone 13 that allows the haptic 32 to flex in a plane perpendicular to the optical axis 22 while maintaining overall rigidity in the vicinity of $W_f$. As illustrated in FIG. 2, the width of the haptic 32 in the vicinity of the flex point $W_f$ is less than the haptic thickness in the vicinity of the flex point $W_f$. Thus, the haptic 32 may flex more in a plane perpendicular to the optical axis 22 than in a plane parallel to the optical axis 22.

In certain embodiments, the peripheral zone 13 is substantially formed by the peripheral face 28, the optic edge 20, and the peripheral portion of the posterior face 18. As illustrated in FIG. 1, the peripheral zone 13 and the buttress 51 form generally rigid structures, the rigidity of the buttress 51 being due, at least in part, to the favorable location of the step edge 39 at the radius $R_1$, on the haptic 32. The location of step edge 39 at a radius $R_1 > R_o$ in combination with the rigidity of the peripheral zone 13 allows the central face 24 to be recessed such that the recessed annular face 30 of the peripheral zone 13 is posterior to the peripheral face 28. This recessed configuration of the central face 24, compared to an optic not having the recessed annular face 30, advantageously reduces the total volume of the intraocular lens 10 by reducing the overall thickness of the optical zone 12. Alternatively, the central face 24 is not recessed, thus increasing the overall rigidity of the intraocular lens 10, but also increasing the total volume of the lens.

As illustrated in FIG. 3, in certain embodiments, the distal posterior face 34 of each haptic 32 is perpendicular to the optical axis 22. In other embodiments, the haptic 32 further comprises an anterior face 58 that is also substantially perpendicular to the optical axis. In such embodiments, the step edge 39 produces an offset relationship between the distal portion 52 of the haptics 32 and the peripheral zone 13. This offset relationship may be favorably used to convert the radial force of the ciliary muscles of the eye on the haptics 32 into an axial force that biases or pushes the posterior face 18 of the optic body 11 in a posterior direction along the optical axis 22 and against the posterior capsule of the eye. This is accomplished without the need for angled haptics, which can be more difficult and/or expensive to manufacture than when the distal posterior face 34, the anterior face 58, or both the distal posterior face 34 and the anterior face 58 are manufactured substantially perpendicular to the optical axis. Alternatively, the haptics 32 may be manufactured such that the distal posterior face 34 and/or the anterior face 58 are disposed at an angle relative to a plane perpendicular to the optical axis 22. This configuration may be used to increase the amount of posterior bias or force on the posterior face 18 of the optic body 11 against the posterior capsule. In such configuration the angle is preferably in the range of about 2 degrees or less to at least about 12 degrees.

In certain embodiments, at least a portion of the peripheral face 28 of the optic body 11 is disposed at an angle θ relative to a plane perpendicular to the optical axis. The angle θ is preferably in the range of about 5 degrees or less to at least about 50 degrees, depending on the dioptric power of the optical zone 12 and the radius of curvature of the posterior face 18 and the central face 24 of the optical zone 12. In one particular embodiment, the angle θ is preferably in the range of about 15 degrees to about 35 degrees, depending upon the dioptric power of the optical zone 12. The angle θ allows the center thickness of and the corresponding lens volume to be reduced by an amount suitable for providing small incision size and insertion force as the intraocular lens moves through the lens inserter.

Figure 4:
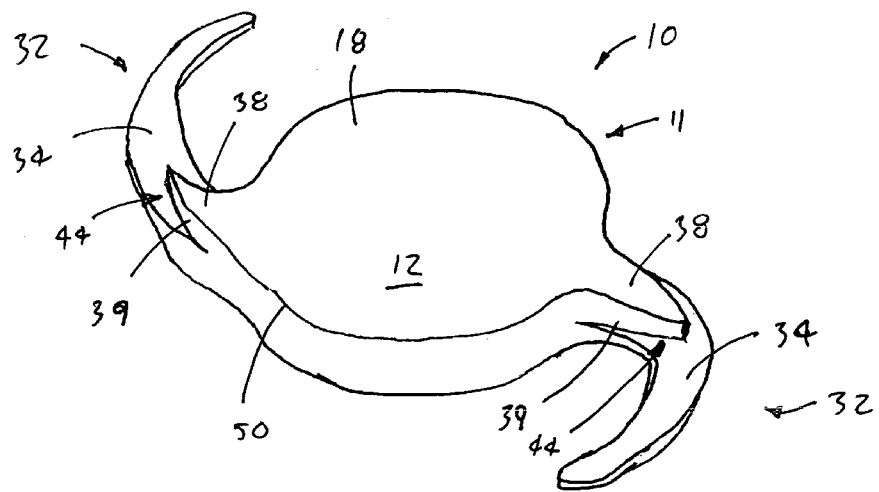
FIG. 4 is a perspective view illustrating the posterior surface of an intraocular lens according to another embodiment of the invention.
Figure 5:
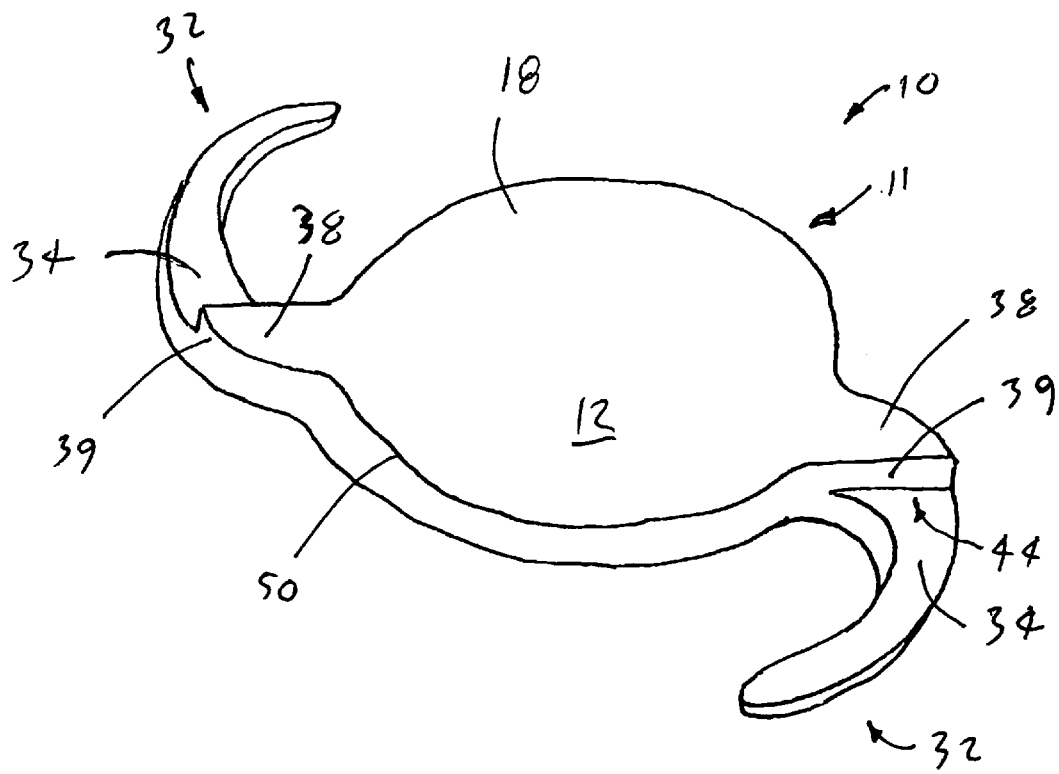
FIG. 5 is a perspective view illustrating the posterior surface of an intraocular lens according to yet another embodiment of the invention.
Figure 6:
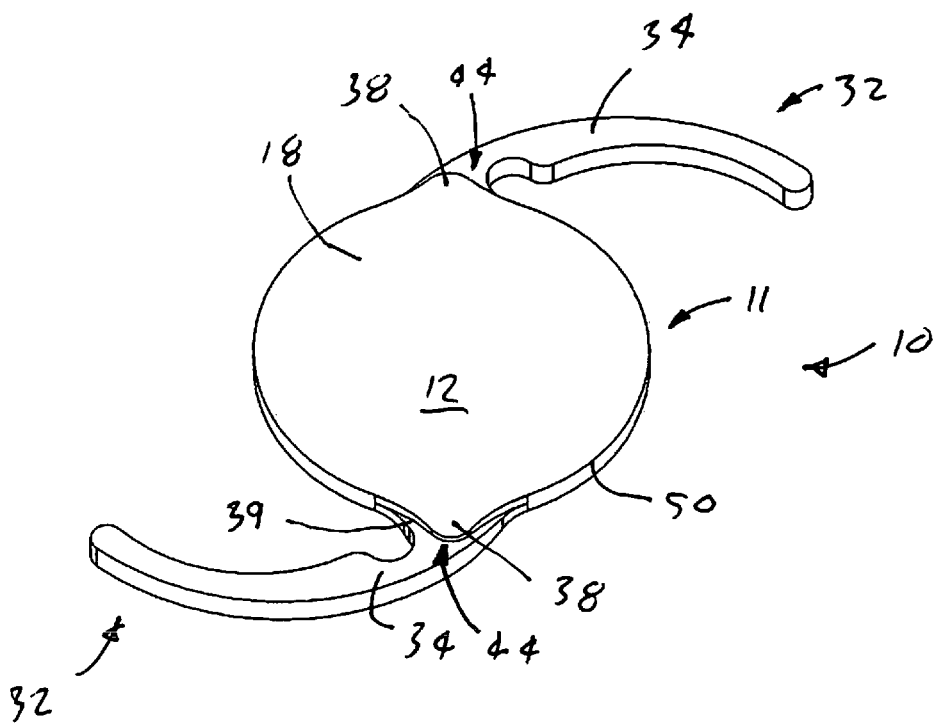
FIG. 6 is a perspective view illustrating the posterior surface of an intraocular lens according to still another embodiment of the invention.

In certain embodiments, as illustrated in FIG. 4 for example, the step edge 39 of the haptic 32 tapers radially. The tapered contour of the step edge 39 serves to elongate the edge corner 50 in the vicinity of the haptics 32. Such shapes may be used to better contact integrity between edge corner 50 and the posterior capsule of the eye, thereby helping to avoid PCO. Other configurations of the step edge 39 may alternatively be used to help maintain the integrity of the contact with the posterior capsule. Referring to FIG. 5, for example, at least a portion of the boundary 44 between the proximal posterior face 38 and the distal posterior face of the haptic 32 may be disposed at an angle such that an opposite side of the step edge conforms to a side of the haptic 32. In other embodiments, as illustrated in FIG. 6, the height H of the step edge 39 may vary along the boundary 44 and/or at least a portion of step edge 39 may form a rounded tip. For instance the height H of the step edge 39 may decrease as the radial distance from the optical axis 22 increases.

Figure 7:
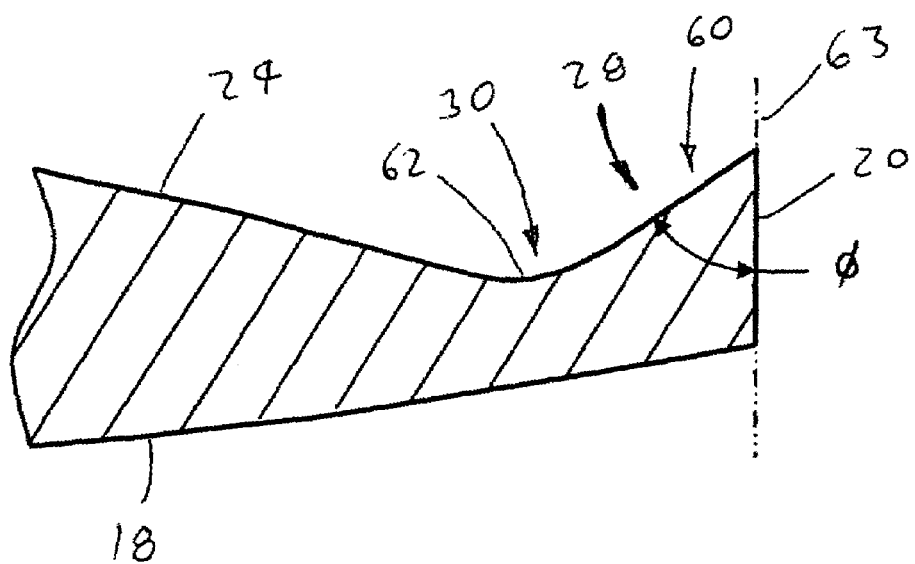
FIG. 7 is a cross-sectional view of a portion of the intraocular lens illustrated in FIGS. 1-3.

FIG. 7 illustrates a cross-sectional view of a portion of the intraocular lens 10. In certain embodiments, the intraocular lens 10 further comprises a cross-sectional profile 60 that is formed by the intersection of a plane passing through the optical axis 22 with the recessed annular face 30 and the peripheral face 28, the cross-sectional profile 60 being continuous, smooth, and free of discontinuities. As used herein, the term "discontinuity" refers to a portion of a profile or surface having a radius of curvature that can scatter light incident thereon. Such discontinuities may be formed, for example, when two portions of a cross-sectional profile that are characterized by different slopes intersect one another. The area of intersection is generally considered as a discontinuity and the inventors have found that such discontinuities, for example as seen in the intraocular lens illustrated in FIG. 3A of U.S. Pat. No. 5,476,513, can contribute to undesired optical effects such as halos or visual poor contrast.

The endpoints of the annular face 30 and the peripheral face 28 along the profile 60 may be defined in various ways. For example, the endpoints of the annular face 30 along the profile 60 may be defined as the points along the profile 60 at which the radius of curvature changes by a certain percentage, for example about 2% or less to about 10% or more, compared to the radius of curvature at the posterior point 62 of the annular face 30. One of the endpoints of the peripheral face 28 along the profile 60 may be defined as the point just prior to the point where the surface normal is perpendicular to the optical axis 22 (e.g., the optic edge 20).

In certain embodiments, as illustrated in FIG. 7, the portion of the profile 60 that is along the peripheral face 28 forms an acute angle $\phi$ with respect to a line 63 that is parallel to the optical axis 22. The inventors have found that by disposing the peripheral face 28 at the acute angle (p, a reduction in unwanted visual effects can be obtained; for example, a reduction in amount of halos and/or a reduction in contrast sensitivity losses. The reason for this enhanced optical performance may be explained as follows. Generally, some of the light entering the eye is refracted by the peripheral face 28 such that it is directed towards and is incident upon the optic edge 20. This portion of refracted light will be referred to as "edge light." Some portion of this edge light is reflected by the optic edge 20, while the remainder of the edge light is transmitted through the optic edge 20. Any edge light that is reflected by the optic edge 20 may ultimately be directed toward or near the fovea, causing one or more of the unwanted visual effects mentioned above. The amount of edge light reflected by the optic edge 20 depends upon the average incidence angle of the rays contained in the edge light relative to the optic edge 20 surface normal. As the average incidence angle of the edge light decreases, the amount of edge light reflected by the optic edge 20 generally decreases. By disposing the peripheral face 28 at the acute angle $\phi$, the edge light is refracted by a greater amount by the peripheral face 28 than if the peripheral face 28 were disposed perpendicular or at an obtuse angle with respect to the line 63. Accordingly, the average incidence angle of the edge light is decreased, meaning that less of the edge light is reflected by the optic edge 20. Thus, less edge light is directed toward or near the fovea and the overall optical performance is advantageously enhanced.

Figure 8:
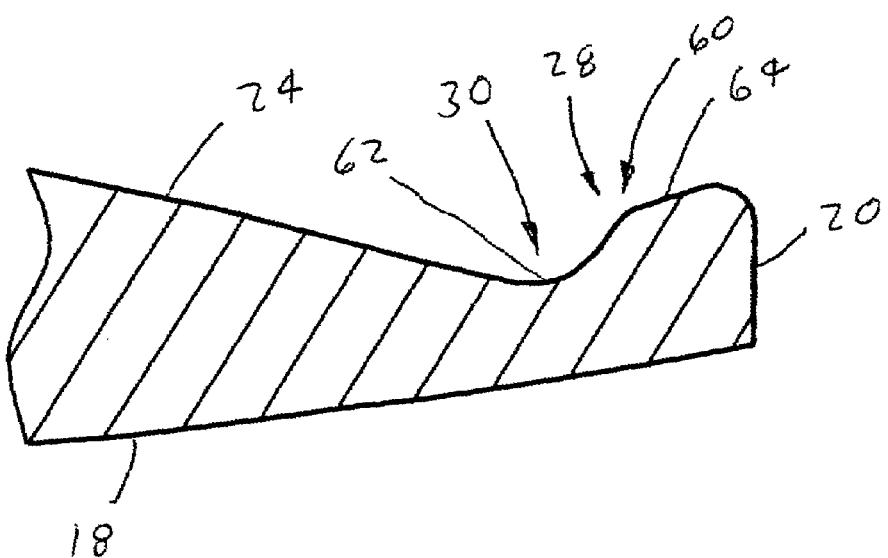
FIG. 8 is a cross-sectional view of an alternative embodiment of the intraocular lens illustrated in FIG. 7.

Referring to FIG. 8, in certain embodiments, the cross-sectional profile 60 further comprises the optic edge 20. In such embodiments, the peripheral face 28 smoothly transitions into the optic edge 20 along the profile 60. Such a smooth transition may be useful to further reduce the amount of unwanted visual effects, as discussed in U.S. Pat. No. 6,468,306 to Paul et al., herein incorporated by reference. The cross-sectional profile 60 preferably consists of a plurality of arcuate sections; however, at least a portion of the cross-sectional profile 60 may comprise a line portion 64 disposed at an acute angle with the optical axis. The line portion 64 preferably forms an acute angle, so as to reduce the amount of light that is internally reflected by the optic edge 20 as discussed above herein.

In certain embodiments, a method of making the foldable intraocular lens 10 comprises providing the optic body 11 having the anterior face 14, the substantially opposing posterior face 18, and the optic edge 20. The method additionally comprises integrally forming the haptics 32 at the peripheral zone 13 to include the distal posterior face 34, a proximal posterior face 38, and a step edge 39. The method also comprises forming the side edge 40 between the optic edge 20 and the step edge 39. The method further comprises forming the proximal posterior face 38 and the posterior face 18 of the optic body 11 into the continuous surface 48. The method additionally comprises forming the edge corner 50 so that it includes the intersection of the continuous surface 48 with the optic edge 20, the side edge 40, and the step edge 39.

The intraocular lens 10 is preferably folded or otherwise compressed for insertion into the capsular bag of an eye via a small incision in the surface of the eye, for example in the cornea, sclera, or the limbus of the eye. Alternatively, the intraocular lens 10 may be placed in front of the capsular bag or even in the anterior chamber of the eye. The incision in the eye is preferably less than about 3.5 mm long, more preferably less than about 3.0 mm long, and even more preferably less than about 2.5 mm to about 2.8 mm long.

The intraocular lens 10 is preferably rolled, folded, or otherwise configured for insertion into the eye through the small incision using forceps, an IOL inserter, or some other suitable device. Once the intraocular lens 10 has been inserted into the eye, the stiffer, more resilient buttress 51 helps to produce a biasing force on the distal portions 52 of the haptics 32, which helps to prevent the haptics sticking to the optic body 11 and helps center the intraocular lens 10 radially and axially.

The intraocular lens may be used alone to replace the natural lens, or to supplement the natural lens or another intraocular lens already inside the eye. The intraocular lens 10 may also be used to provide accommodation lost due to presbyopia or loss of the natural lens. In such uses, the intraocular lens 10 may be either as a solitary lens or use as part of a lens system. The haptics 34 may also be replaced by or supplemented with a more complex positioning structure.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A foldable intraocular lens, comprising:
   an optic body including an optical zone and a peripheral zone entirely surrounding the optical zone, the optic body having an anterior face, a substantially opposing posterior face, an optic edge, and an optical axis, the anterior face comprising a central face, a peripheral face, and a recessed annular face therebetween disposed posterior to the peripheral face, the recessed annular face encircling the optical axis;

at least one haptic integrally formed with the peripheral zone, comprising:
a distal posterior face and a proximal posterior face; and
a boundary between the proximal posterior face and the distal posterior face, the distal posterior face being offset at the boundary from the proximal posterior face in a direction along the optical axis;

the proximal posterior face and the posterior face of the optic body forming a continuous surface;

an edge corner comprising an intersection of the continuous surface with the optic edge and the boundary.

2. The foldable intraocular lens of claim 1, wherein the distal posterior face is substantially perpendicular to the optical axis.

3. The foldable intraocular lens of claim 1, wherein the haptic is characterized by a haptic thickness equal to a distance along the optical axis between the distal posterior face and a substantially opposing haptic anterior face.

4. The foldable intraocular lens of claim 3, wherein the haptic thickness is greater than or approximately equal to an optic edge thickness of the optic edge along the optical axis.

5. The foldable intraocular lens of claim 3, wherein at least one of the haptic thickness or the optic edge thickness along the optical axis is in the range of at about 0.2 mm or less to about 1 mm or more.

6. The foldable intraocular lens of claim 3, wherein at least one of the haptic thickness or the optic edge thickness along the optical axis is in the range of about 0.4 mm to about 0.5 mm.

7. The foldable intraocular lens of claim 1, wherein the boundary has a height H and the optic edge has a thickness T.

8. The foldable intraocular lens of claim 7, wherein the height H is less than the thickness T.

9. The foldable intraocular lens of claim 7, wherein the height H is greater than or approximately equal to the thickness T.

10. The foldable intraocular lens of claim 7, wherein the height H is about 0.1 mm.

11. The foldable intraocular lens of claim 7, wherein the thickness T is in the range of about 0.4 mm to about 0.5 mm.

12. The foldable intraocular lens of claim 1, wherein the distal posterior face is disposed at an angle relative to a plane perpendicular to the optical axis.

13. The foldable intraocular lens of claim 12, wherein the angle is in the range of at least about 2 degrees to at about 12 degrees or greater.

14. The foldable intraocular lens of claim 1, wherein at least a portion of the peripheral face is disposed at an angle relative to a plane perpendicular to the optical axis.

15. The foldable intraocular lens of claim 14, wherein, the angle being in the range of about 5 degrees to at least about 50 degrees.

16. The foldable intraocular lens of claim 14, wherein, the angle being in the range of about 15 degrees to about 35 degrees.

17. The foldable intraocular lens of claim 1, wherein at least a portion of the boundary forms a substantially straight line.

18. The foldable intraocular lens of claim 1, wherein the boundary has a height that is in the range of about 0.05 mm or less to about 1 mm or more.

19. The foldable intraocular lens of claim 1, wherein the boundary has a height that is in the range of about 0.05 mm to at least about 0.2 mm.

20. The foldable intraocular lens of claim 1, wherein the boundary has a height that is in the range of about 0.2 mm to about 0.5 mm.

21. A foldable intraocular lens, comprising:
an optic body including an optical zone and a peripheral zone entirely surrounding the optical zone, the optic body having an anterior face, a substantially opposing posterior face, an optic edge, and an optical axis;
at least one haptic integrally formed with the peripheral zone, comprising:
a distal posterior face and a proximal posterior face; and
a boundary between the proximal posterior face and the distal posterior face, the distal posterior face being offset from the proximal posterior face at the boundary in a direction along the optical axis;
the proximal posterior face and the posterior face of the optic body forming a continuous surface;
an edge corner comprising an intersection of the continuous surface with the optic edge and the boundary;
the distal posterior face being perpendicular to the optical axis along a finite radial length.

22. The intraocular lens of claim 21, wherein the haptic further comprises an anterior face that is perpendicular to the optical axis.

23. A method of making a foldable intraocular lens, comprising:
providing an optic body including an optical zone and a peripheral zone entirely surrounding the optical zone, the optic body having an anterior face, a substantially opposing posterior face, an optic edge, and an optical axis, the anterior face comprising a central face, a peripheral face, and a recessed annular face therebetween disposed posterior to the peripheral face, the recessed annular face encircling the optical axis;
at the peripheral zone, integrally forming at least one haptic comprising a distal posterior face, a proximal posterior face, and a boundary therebetween, the distal posterior face being offset at the boundary from the proximal posterior face in a direction along the optical axis;
forming the proximal posterior face and the posterior face of the optic body into a continuous surface;
forming an edge corner comprising an intersection of the continuous surface with the optic edge and the boundary.

24. The method of claim 23, wherein the distal posterior face being substantially perpendicular to the optical axis.

25. A foldable intraocular lens, comprising:
an optic body disposed about an optical axis and comprising an optical zone and a peripheral zone disposed about the optical zone, the peripheral zone having an outer radius of curvature, the optic body having an anterior face, an opposing posterior face, and a wall face disposed between the anterior face and the posterior face, the anterior face comprising a central face, a peripheral face, and a recessed annular face therebetween disposed posterior to the peripheral face, the recessed annular face entirely surrounding a point along the optical axis;
at least one haptic integrally formed with the peripheral zone, comprising:
a distal posterior face and a proximal posterior face; and
a step boundary between the proximal posterior face and the distal posterior face, the distal posterior face being offset at the step boundary from the proximal posterior face in a direction along the optical axis;

a continuous surface comprising the proximal posterior face and the posterior face of the optic body; and an outer boundary edge comprising an edge corner, and the outer boundary surrounding the continuous surface and comprising the step boundary and an intersection of the continuous surface with the wall face.

* * * * *

UNITED STATES PATENT AND TRADEMARK OFFICE
CERTIFICATE OF CORRECTION

PATENT NO.        : 7,621,949 B2                                                Page 1 of 1
APPLICATION NO.   : 11/010003
DATED             : November 24, 2009
INVENTOR(S)       : Deacon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1349 days.

Signed and Sealed this

Fourteenth Day of December, 2010

David J. Kappos
*Director of the United States Patent and Trademark Office*